US009788560B2

(12) United States Patent
Toomey et al.

(10) Patent No.: US 9,788,560 B2
(45) Date of Patent: Oct. 17, 2017

(54) SUPPLEMENTAL FOOD

(71) Applicant: New Chapter, Inc., Cincinnati, OH (US)

(72) Inventors: Jennifer Marie Toomey, Brattleboro, NJ (US); Graham Rigby, Brattleboro, NJ (US); Paul Schulick, Brattleboro, NJ (US)

(73) Assignee: The Procter & Gamble Company, Cincinnati, OH (US)

( * ) Notice: Subject to any disclaimer, the term of this patent is extended or adjusted under 35 U.S.C. 154(b) by 0 days.

(21) Appl. No.: 14/656,736

(22) Filed: Mar. 13, 2015

(65) Prior Publication Data
US 2015/0257425 A1 Sep. 17, 2015

Related U.S. Application Data

(60) Provisional application No. 61/953,105, filed on Mar. 14, 2014.

(51) Int. Cl.
A61K 36/61 (2006.01)
A61K 36/82 (2006.01)
A61K 36/53 (2006.01)
A61K 36/9068 (2006.01)
A23L 1/30 (2006.01)
A61K 36/906 (2006.01)
A61K 36/185 (2006.01)
A61K 36/324 (2006.01)
A61K 36/28 (2006.01)
A61K 36/9066 (2006.01)
A23K 20/158 (2016.01)
A23K 20/10 (2016.01)
A23K 50/40 (2016.01)
A23L 33/105 (2016.01)

(52) U.S. Cl.
CPC ............ *A23L 1/3002* (2013.01); *A23K 20/10* (2016.05); *A23K 20/158* (2016.05); *A23K 50/40* (2016.05); *A23L 33/105* (2016.08); *A61K 36/185* (2013.01); *A61K 36/28* (2013.01); *A61K 36/324* (2013.01); *A61K 36/53* (2013.01); *A61K 36/61* (2013.01); *A61K 36/82* (2013.01); *A61K 36/906* (2013.01); *A61K 36/9066* (2013.01); *A61K 36/9068* (2013.01); *A23V 2002/00* (2013.01)

(58) Field of Classification Search
USPC ................ 424/747, 745, 756, 764, 729, 777
See application file for complete search history.

(56) References Cited

U.S. PATENT DOCUMENTS 6,264,995 B1 7/2001 Newmark et al.
6,387,416 B1 5/2002 Newmark et al.
6,391,346 B1* 5/2002 Newmark ............ A61K 36/185 424/733
6,541,045 B1* 4/2003 Charters .............. A61K 36/185 424/725
7,067,159 B2 6/2006 Newmark et al.
7,070,816 B2 7/2006 Newmark et al.
7,563,462 B2* 7/2009 Newmark ............. A61K 36/29 424/725
7,622,142 B2 11/2009 Newmark et al.
7,744,931 B2 6/2010 Newmark et al.
7,744,934 B2 6/2010 Newmark et al.
8,017,147 B2 9/2011 Mazed et al.
8,092,845 B2* 1/2012 Tikhonov ............. A61K 31/355 424/756
8,114,446 B2 2/2012 Newmark et al.
2002/0136782 A1* 9/2002 Fleischner ........... A61K 31/137 424/725
2004/0142049 A1* 7/2004 Mae ..................... A61K 36/484 424/739
2005/0058728 A1 3/2005 Randolph et al.
2007/0041276 A1 2/2007 Jansen et al.
2009/0004334 A1 1/2009 Nair
2010/0150865 A1 6/2010 Chitre et al.
2011/0200689 A1 8/2011 Newmark et al.
2011/0262552 A1* 10/2011 Chamberland ...... A61K 36/185 424/547

FOREIGN PATENT DOCUMENTS

FR WO 2012039745 A1 * 3/2012 ........... A23K 1/1618
WO WO 01/15553 A1 3/2001
WO WO 02/063982 A1 8/2002
WO WO 2006/010606 A1 2/2006
WO WO 2008/120220 A1 10/2008
WO WO 2010/138003 A1 12/2010

OTHER PUBLICATIONS

Raventos et al. Application and Possibilities of Supercritical CO2 Extraction in Food Processing Industry: An Overview, Food Science Tech. Int. 2002;8(5):269-279).*
Ocana et al. Effects of Thyme Extract Oils (fromThymus vulgaris, Thymus zygis, and Thymus hyemalis) on Cytokine Production and Gene Expression of oxLDL-Stimulated THP-1-Macrophages (Journal of Obesity vol. 2012, Article ID 104706, 11 pages).*
International Search Report and Written Opinion for 13257—PCT/US2015/020416 dated Mar. 13, 2015.
Philippou, Y, et al. "Complementary and alternative medicine (CAM) in prostate and bladder cancer", BJU International, 2013.
Kunnumakkara, A.B. et al., "Zyflamend suppresses growth and sensitizes human pancreatic tumors to gemcitabine in an orthotopic mouse model through modulation of multiple targets", International Journal of Cancer, 131(3), pp. E292-E303, 2012.

(Continued)

*Primary Examiner* — Chris R Tate
*Assistant Examiner* — Deborah Davis
(74) *Attorney, Agent, or Firm* — Amanda Herman; Alexandra S. Anoff

(57) ABSTRACT

Supplements for maintaining a healthy immune response include one or more extracts from rosemary, turmeric, green tea, ginger, holy basil, oregano, boswellia, black currant, and clove. The supplements may include an extract of thyme. The supplements may exclude anti-inflammatory drugs and certain anti-inflammatory herbs.

11 Claims, No Drawings

(56) References Cited

OTHER PUBLICATIONS

Huang, E.C. et al., "Zyflamend, a combination of herbal extracts, attenuates tumor growth in murine xenograft models of prostate cancer", Nutrition and Cancer, 64(5), pp. 749-760, 2012.
Mohebati, A., et al. "Carnosol, a constituent of zyflamend, inhibits aryl hydrocarbon receptor medicated activation of CYP1A1 and CYP1B1 transcription and mutagenesis", Cancer Prevention Research, 5(4), pp. 593-602, 2012.
Kim, J.H. et ap. "Zyflamend sensitizes tumor cells to TRAIL induced apoptosis through up regulation of death receptors and down regulation of survival proteins: Role of ROS dependent CCAAT/enhancer-binding protein-homologous protein pathway", Antioxidaants and Redox Signaling, 16(5), pp. 413-427, 2012.
Yan, J. et al. "Zyflamend inhibits the expression and function of androgen receptor and acts synergistically with bicalutimide to inhibit prostate cancer cell growth", Prostate, 72(3) pp. 244-252, 2012.
Bostwick, D.G. et al. "Precursors of prostate cancer", Histopathology, 60(1), pp. 4-27, 2012.
Huang, E.C., "Zyflamend reduces the expression of androgen receptor in a model of castrate resistant prostate cancer", Nutrition and Cancer, 63(8), pp. 1287-1296, 2011.
Ekmekcioglu, S., et al. "Zyflamend mediates therapeutic induction of autophagy to apoptosis in melanoma cells", Nutrition and Cancer, 63(6), pp. 940-949, 2011.
Rosenbaum, C.C., et al. "Antioxidants and anti-inflammatory dietary supplements for osteoarthritis and rheumatoid arthritis", Alternative Therapies in Health and Medicine, 16(2), pp. 32-40, 2010.
Capodice, J.L., "Zyflamend in men with high grade prostatic intraepithelial neoplasia: Results of a phase I clinical trial", Journal of the Society for Integrative Oncology, 7(2), pp. 43-51, 2009.
Yang, P., et al. "Zyflamend® reduces LTB4 formation and prevents oral carcinogenesis in a 7,12-dimethylbenz(a)anthracene (DMBA) induced hamster cheek pouch model", Carcinogenesis, 29(11), pp. 2182-2189, 2008.
Goel, A, et al. "Curcumin as Curecumin: From kitchen to clinic", Biochemical Pharmacology, 75(4), pp. 787-809, 2008.
Sandur, S.K., et al., "Zyflamend, a polyherbal preparation, inhibits invasion, suppresses osteoclastogenesis, and potentiates apoptosis through down regulation of NF-kB Activation and NF kB regulated gene products", Nutrition and Cancer, 57(1), pp. 7887, 2007.
Rafailov, S. et al., "The role of zyflamend, an herbal anti-inflammatory, as a potential chemopreventive agent against prostate cancer: A case report", Integrative Cancer Therapies, 6(1), pp. 74-76, 2007.
Block, K.I., "Editorial: Just in cases", Integrative Cancer Therapies, 6(91), pp. 5-7, 2007.
Yang, P. et al., "Zyflamend® mediated inhibition of human prostate cancer PC3 cell proliferation: Effects on 12 LOX and Rb protein phosphorylation", Cancer Biology and Therapy, 6(2), pp. 228-236, 2007.
Nelson, M.A., "Inhibition of lipoxygenase activity: Implications for the treatment and chemoprevention of prostate cancer", Cancer Biology and Therapy, 6(2), p. 237, 2007.
Bemis, D.L. et al., "Clinical trials of natural products as chemopreventive agents for prostate cancer", Expert Opinion on Investigational Drugs, 15(10), pp. 1191-1200, 2006.
"Integrative medicine news update", Evidence Based Integrative Medicine 2(2), pp. 101-110, 2005.
Bemis, D.L. et al., "Zyflamend® a unique herbal preparation with nonselective COX inhibitory activity, induces apoptosis of prostate cancer cells that lack COX-2 expression", Nutrition and Cancer 52(2), pp. 202-212, 2005.
Dietary Supplement for Inflammation and Heart Health from New Chapter, Feb. 2012—located at http://www.gnpd.com/sinatra/recordpage/1741287/from_search/UUQDG1uPuN/.

* cited by examiner

SUPPLEMENTAL FOOD

FIELD OF THE INVENTION

This invention relates generally to food supplements or supplemental food for mammals, especially, but not exclusively, humans.

BACKGROUND OF THE INVENTION

Practicing good nutrition is challenging. Even with an understanding of the current nutritional science, it can be difficult to follow a well-designed diet regularly. In addition to lapses in discipline, specific foods or foods which are good sources of a particular nutrient may be unavailable or inconvenient when needed. These challenges are compounded when attempting to obtain the benefit of helpful interactions between different foods or different nutrients.

Nutritional supplements have evolved, first from general vitamin and mineral supplements based on Recommended Daily Allowances (RDA) generally determined by studying different nutrients in isolation, to more sophisticated general vitamin and mineral supplements, to "supplemental foods" or "food supplements". Whole-food supplementation seeks to provide the nutritional benefits of a food (as opposed to an isolated nutrient, which might be derived from a food, or synthesized or isolated from a non-food product) without the volumetric or caloric intake of consuming the food itself. This approach permits convenient, concentrated nutrient uptake in a form that mimics the mixture of nutrients found in a whole food, and, therefore, the helpful interactions between different nutrients that naturally occur in a particular food.

Nutrient interactions have been the subject of extensive study over the last 25 years, but are still a highly unpredictable field. Extrapolations from interactions between individual nutrients to classes of nutrients often fail, sometimes with no synergy observed for closely related class members, and sometimes with deleterious effects when substituting one nutrient for another class member. A supplemental food approach may help reduce variability in response by preserving naturally occurring interactions. Of course, even with a supplemental food approach, removing bulk and calories from a food necessarily involves decisions about extraction and processing that can unintentionally change the types and relative amounts of nutrients in a supplement, which can, in turn, unintentionally change the presence or degree of the nutritional benefit of the supplement. These challenges, too, are exacerbated when a supplement aims to provide the benefit of multiple food components, e.g., to mimic benefits from consuming several types of foods together. Ayurvedic medicine, for example, addresses hundreds of herbs which may be helpful for maintaining or restoring health, often used in combinations of 3 or more herbs.

There remains a need for dietary supplements which provide specific combinations of nutrients in desirable ratios. There remains a need for dietary supplements which support specific aspects of health and well-being.

SUMMARY OF THE INVENTION

In some aspects, the invention relates to a supplement for maintaining healthy immune response. The supplement may comprise an extract of rosemary. The supplement may comprise an extract of turmeric. The supplement may comprise an extract of green tea. The supplement may comprise an extract of ginger. The supplement may comprise an extract of holy basil. The supplement may comprise an extract of oregano. The supplement may comprise an extract of black currant. The supplement may comprise an extract of clove. The supplement may comprise an extract of thyme. The extract of thyme may be a supercritical extract. The supplement may be suitable for oral administration. The extract of holy basil may comprise a supercritical extract and an ethanolic extract. The extract of turmeric may include supercritical extract and hydroethanolic extract in a ratio between 1:3 and 1:5, or in a ratio of about 1:4. The supplement may comprise an extract of chamomile. The extract of oregano may include supercritical extract and hydroethanolic extract. The extract of oregano may include supercritical extract and hydroethanolic extract in a ratio of about 1:1. The supplement may comprise boswellia *serrata*.

In some aspects, the invention relates to a method of moderating the inflammatory response to a transient pro-inflammatory stimulus, comprising administering a supplement comprising extracts of rosemary, turmeric, green tea, ginger, holy basil, oregano, black currant, and clove, optionally with an extract of thyme or chamomile, to a mammal prior to the mammal encountering a transient pro-inflammatory stimulus. The transient pro-inflammatory stimulus may be exercise, an allergen, or a transient increase in oxidative stress.

In some aspects, the invention relates to a supplement for maintaining healthy immune response. The supplement may comprise an extract of rosemary. The supplement may comprise an extract of turmeric. The supplement may comprise an extract of green tea. The supplement may comprise an extract of ginger. The supplement may comprise an extract of holy basil. The supplement may comprise an extract of oregano. The supplement may comprise an extract of black currant. The supplement may comprise an extract of clove. The supplement may comprise an extract of boswellia *serrata*. The supplement may comprise an extract of chamomile. The supplement may comprise an extract of thyme. The extract of thyme may be a supercritical extract. The supplement may be suitable for oral administration. The extract of holy basil may comprise a supercritical extract and an ethanolic extract. The extract of turmeric may include supercritical extract and hydroethanolic extract in a ratio between 1:3 and 1:5, or in a ratio of about 1:4. The extract of oregano may include supercritical extract and hydroethanolic extract. The extract of oregano may include supercritical extract and hydroethanolic extract in a ratio of about 1:1.

In some aspects, the invention relates to a method of moderating the inflammatory response to a transient pro-inflammatory stimulus, comprising administering a supplement comprising extracts of rosemary, turmeric, green tea, ginger, holy basil, oregano, black currant, clove, and boswellia *serrata*, optionally with an extract of thyme or chamomile, to a mammal prior to the mammal encountering a transient pro-inflammatory stimulus. The transient pro-inflammatory stimulus may be exercise, an allergen, or a transient increase in oxidative stress.

DETAILED DESCRIPTION OF THE INVENTION

As used herein, the term "supplement" refers to a composition intended to supplement a diet of food and water, where the diet is sufficient to support life. A supplement may contain vitamins, minerals, herbs or other botanicals, amino acids, enzymes, organ tissues, glandular metabolites, or combinations thereof. A supplement may be an extract or concentrate of a particular food source or a particular nutrient. Supplements may be administered by any convenient means, including parenteral or enteral routes. Enteral routes may include oral, gastric, or subgastric administration, including rectal administration.

In a preferred form, the supplements of the present invention are administered orally. Oral administration forms include, without limitation, tablets, capsules, softgels, gelcaps, liquids, powders, and films, as well as food-like forms such as bars, candies, lozenges, beverages, and the like.

As used herein, the term "supercritical gas" or "supercritical fluid" refer to a gas is that heated to a temperature critical point, over which the gas will maintain its gaseous state and not turn to a liquid regardless of pressure. A gas heated to a temperature above its critical point will become very dense on compression, so that its characteristics resemble those of a fluid, but will not become liquid. Carbon dioxide is commonly used in applications requiring a supercritical fluid. The general properties of supercritical fluids and the general use of supercritical fluids in extraction processes are described in, e.g. Taylor, Supercritical Fluid Extraction, Wiley, 1996; McHugh and Krukonis, Supercritical Fluid Extraction: Principles and Practice, 2nd ed., Butterworth-Heinemann, 1994; and Williams and Clifford, Supercritical Fluid Methods and Protocols, Humana Press, 2000.

As used herein, the term "supercritical extraction" refers to the technique in which hydrophobic compounds can be extracted from samples utilizing a supercritical fluid. The solvation power of a supercritical fluid is increased as the pressure and temperature are increased above their critical points, producing an effective solvent for the isolation of hydrophobic molecules.

As used herein, the terms "hydroalcoholic extraction" or "hydroethanolic extraction" refer to the technique in which hydrophilic compounds can be extracted from a sample utilizing a solution of alcohol and water, followed by evaporation of the solution to produce an extract consisting of dissolved solids. In the case of hydroethanolic extraction, the alcohol can be ethanol.

As used herein, the term "mammal" refers to any vertebrate of the class Mammalia. The term "mammal" includes the sub-classes of humans and companion animals. "Companion animals," as used herein, include dogs and cats of all ages (e.g., puppies or kittens, adults between 1 and 6 years of age, seniors between 7 and 10 years of age, and super-seniors 11 years of age or older), and other mammals of like nutritional needs to dogs and cats. For example, other domesticated animals of like nutritional needs to a cat may include minks and ferrets, who can survive indefinitely and healthily on a nutritional composition designed to meet the nutritional needs of cats. It will be appreciated by one of skill in the art that dogs and cats have nutritional needs which differ in key aspects. At a fundamental level, dogs are omnivores, whereas cats are obligate carnivores. Further, nutritional needs are not necessarily consistent with phylogenetic or other non-nutritional classifications.

As used herein, "complete and nutritionally balanced" refers to a composition that provides all of a typical animal's nutritional needs, excepting water, when fed according to feeding guidelines for that composition, or according to common usage, if no feeding guidelines are provided. Such nutritional needs are described, for example, in Nutrient Profiles for dogs and cats published by the Association of American Feed Control Officials (AAFCO).

The inventive composition is a mixture comprised of herbal extracts. The compositions may moderate inflammatory processes. As used herein, "moderate" refers to a chemically measurable change in one or more physiological markers of inflammation. In humans, moderation of inflammatory processes may be measured by self-reporting of symptoms of inflammation, such as pain or swelling. In non-human mammals or humans who cannot communicate effectively about their inflammatory symptoms, moderation of inflammatory processes may be measured from reports from a care provider regarding physical signs of inflammation, such as perceived tenderness, pain, swelling, or range or ease of motion. In any mammal, moderation of inflammatory processes may be measured by biochemical analysis of tissue or fluid samples, such as samples of skin, blood, tears, or other body tissues or fluids. Suitable biomarkers for comparison and analysis include pro-inflammatory cytokines (such as IL-1B, IL-6, IL-8, MIP-1$\alpha$, and TNF$\alpha$), 5-lipoxygenase, 12-lipoxygenase, Leukotriene B4 (LTB4) receptors, Prostaglandin E2 (PGE2), NF-k$\beta$, COX peroxidase activity, and combinations thereof. It is not necessary to see a change in all relevant biomarkers to obtain effective moderation of an inflammatory response.

The compositions may help maintain or support a healthy immune response. For example, the compositions may help moderate normal, short-term increases in inflammation, such as those that may follow exercise or other physical activity.

The compositions are unique in the herbs selected, in the combinations and ratios thereof, in the synergies and activities amongst the herbs, and in that they are prepared via a supercritical $CO_2$ extraction process. Unlike traditional solvent based extraction methods, supercritical $CO_2$ extraction allows the natural products in the herbs to be obtained without leaving chemical residues behind in the preparation. A combination of extracts from hydroalcoholic extraction and supercritical CO2 extraction can produce a constituent profile similar to the native herb in a more concentrated state.

Supercritical extraction can be performed according to known supercritical extraction methods, such as disclosed, e.g., in E. Stahl, K. W. Quirin, D. Gerard, Dense Gases for Extraction and Refining, Springer Verlag 4 1988. The plant, or suitable portion thereof, such as, for example, the rhizome in the case of ginger, which can be cryogenically ground to preserve heat sensitive components, is subjected to supercritical extraction to obtain: (i) an oil extract, referred to herein as "the supercritical extract" of the plant, containing delicate lipophilic components, and (ii) an oil-free residue. The oil-free residue can then be extracted in a water/alcohol, for example, water/ethanol, mixture composed of 60-80 parts alcohol and 40-20 parts water. The alcohol/water liquid is then evaporated off, leaving a powdered extract residue, referred to herein as "the hydroalcoholic extract" of the plant. Alternatively, the supercritical extraction and the hydroalcoholic extraction can be performed on separate batches of plant material.

The hydroalcoholic extraction can be performed according to conventional hydroalcoholic extraction techniques. For example, the hydroalcoholic extracts can be prepared by extracting the plant portion in a water/alcohol, such as, for example, water/ethanol, mixture that can be composed of 60-80 parts alcohol and 40-20 parts water, and then evaporating off the water/alcohol liquid, leaving a powdered extract residue referred to herein as "the hydroalcoholic extract". In certain embodiments, the water/alcohol liquid mixture can be evaporated at a temperature ≤80° C., such as, for example, by utilizing a spray-drying technique, leaving a powdered extract residue.

Some extracts, such as green tea extract, are obtained by water-only extraction.

Examples

| Active Ingredient | Ex. 1 mg | Ex. 2 mg | Ex. 3 mg | Ex. 4 mg |
|---|---|---|---|---|
| Rosemary (SCE & HE) | 150 | 150 | 150 | 150 |
| Rosemary SCE | 100 | 100 | 100 | 100 |
| Rosemary HE | 50 | 50 | 50 | 50 |
| Turmeric (SCE and HE) | 110 | 125 | 110 | 110 |
| Turmeric SCE | 10 | 25 | 22 | 22 |
| Turmeric HE | 100 | 100 | 88 | 88 |
| Green Tea | 100 | 100 | 100 | 100 |
| Ginger (SCE & HE) | 100 | 75 | 100 | 100 |
| Ginger SCE | 54 | 15 | 54 | 54 |
| Ginger HE | 46 | 60 | 46 | 46 |
| Holy Basil (SCE & HE) | 100 | 50 | 50 | 50 |
| Holy Basil SCE | —* | 8 | 8 | 8 |
| Holy Basil HE | 100 | 42 | 42 | 42 |
| Chamomile (SCE & HE) | — | 15 | — | — |
| Chamomile SCE | — | 4 | — | — |
| Chamomile HE | — | 11 | — | — |
| Oregano (SCE & HE) | 40 | 20 | 20 | 20 |
| Oregano SCE | 40 | 10 | 10 | 10 |
| Oregano HE | — | 10 | 10 | 10 |
| *Boswellia serrata* | — | 150 | — | 100 |
| Black currant | — | 30 | 30 | 50 |
| Clove SCE | — | 7 | 7 | 7 |
| Hu Zhang (*Polygonum cuspidatum*) (root and rhizome) HE | 80 | — | — | — |
| Chinese Goldthread (*Coptis chinesis*) (root) HE | 40 | — | — | — |
| Barberry (*Berberis vulgaris*) (root) HE | 40 | — | — | — |
| Chinese Skullcap (*Scutellaria baicalensis*) (root) HE | 20 | — | — | — |
| Thyme SCE | — | — | 10 | 5 |

*Throughout this chart,
"—" indicates no addition (zero content) of a particular ingredient in a particular example.

In preparation for the following seven assays, pre-encapsulated formulas according to Examples 1-4 were dissolved in dimethyl sulfoxide (DMSO) and evaluated at semi-log dilutions of 100, 30, 10, 1, 0.1, and 0.03 μg/mL.

Cytokine Panel

Human Peripheral Blood Mononuclear Cells (PBMCs) from 3 different donors are exposed to Lipopolysaccharide (LPS) to stimulate secretion of inflammatory agents IL-1b, IL-6, IL-8, MIP-1α and TNFa. Levels of cytokines are detected through luminex quantitation and inhibition by Zyflamend formulations is reported as pg/mL for the strength of the response. The positive control for this assay is Dexamethasone.

Donors used for this trial include a female, Caucasian, age 30-40 yrs; a male, Mixed Asian, age 30-40 yrs; and a male, African American, age 50-60 yrs. Increased percent inhibition is preferred.

| Inflammatory Agent | Total Active Concentration | Results |
|---|---|---|
| IL-1B | 10 ug/ml | Percent inhibition of IL-1B was higher for each of Examples 3-4 than for Example 1. Percent inhibition of IL-1B was higher for Example 2 than for Example 1 in PBMCs from 2 of the 3 donors. The percent inhibition of Example 2 was lower than for Example 1 in PBMCs from the African American donor; it is unclear whether this result is related to individual variance or a possible difference in ethnic/racial or age group response to Example 2. |
| | 30 ug/ml | Percent inhibition of IL-1B was higher for each of Examples 3-4 than for Example 1. Percent inhibition of IL-1B was higher for Example 2 than for Example 1 in PBMCs from 2 of the 3 donors. The percent inhibition of Example 2 was lower than for Example 1 in PBMCs from the African American donor; it is unclear whether this result is related to individual variance or a possible difference in ethnic/racial or age group response to Example 2. |
| IL-6 | 10 ug/ml | Percent inhibition of IL-6 was higher for each of Examples 3-4 than for Example 1. Percent inhibition of IL-8 was higher for Example 2 than for Example 1 in PBMCs from 2 of the 3 donors. The percent inhibition of Example 2 was comparable to or lower than Example 1 in PBMCs from the donor of Mixed Asian ancestry, although it is unclear whether this result is related to individual variance or a possible difference in ethnic/racial group response to Example 2. |
| | 30 ug/ml | Percent inhibition of IL-6 was higher for each of Examples 2-4 than for Example 1. |
| IL-8 | 10 ug/ml | Percent inhibition of IL-8 was higher for each of Examples 3-4 than for Example 1. Percent inhibition of IL-8 was higher for Example 2 than for Example 1 in PBMCs from 2 of the 3 donors. The percent inhibition of Example 2 was comparable to Example 1 in PBMCs from the donor of Mixed Asian ancestry, although it is unclear whether this result is related to individual variance or a possible difference in ethnic/racial group response to Example 2. |
| | 30 ug/ml | Percent inhibition of IL-8 was higher for each of Examples 2-4 than for Example 1. |
| MIP-1A | 10 ug/ml | Percent inhibition of MIP-1A was higher for each of Examples 2-4 than for Example 1. |
| | 30 ug/ml | Percent inhibition of MIP-1A was higher for each of Examples 2-4 than for Example 1. |
| TNF-α | 10 ug/ml | Percent inhibition of TNF-α was higher for each of Examples 2-4 than for Example 1. |
| | 30 ug/ml | Percent inhibition of TNF-α was higher for each of Examples 2-4 than for Example 1. |

Surprisingly, the variations in the compositions of Examples 2-4 provided generally improved pro-inflammatory cytokine inhibition compared to Example 1, even though all of the ingredients of Example 1 are known (in traditional medicine and/or the scientific literature) as anti-inflammatory agents. The relatively better performance of Examples 3-4 relative to Example 2 further suggest that the addition of a supercritical extract of Thyme, even at low inclusion levels, may help reduce pro-inflammatory cytokine response. Further, the similar performance of Examples 3-4 suggest that boswellia is not a critical ingredient for reducing pro-inflammatory cytokine response, at least among the cytokines studied here. This is surprising, since boswellia is considered a medicinal herb, and thyme is generally considered a culinary herb.

5 Lipoxygenase

5-Lipoxygenase catalyzes the oxidative metabolism of arachidonic acid to 5-hydroxyeicosatetraenoic acid (5-HETE), the initial reaction leading to formation of leukotrienes. Human recombinant 5-Lipoxygenase expressed in insect sf9 cells is used. Test compound and/or vehicle is preincubated with 5 U/ml enzyme‡ in Tris buffer for 15 minutes at 25° C. The reaction is initiated by addition of 3 µM Arachidonic acid for another 5 minute incubation period and is terminated by further addition of 1 N HCl. An aliquot is removed and determined the amount of Leukotriene B4 (LTB$_4$) formed spectrophotometrically by Enzyme ImmunoAssay (EIA) kit. Compounds are screened at 10 µM. Nordihydroguaiaretic acid (NDGA) is used as the standard reference for this assay.

At 10 and 30 ug/ml, the percent inhibition of 5-lipoxygenase was comparable for all of Examples 1-4.

12 Lipoxygenase

12-Hydroxyeicosatetraenoic acid (12-HETE) is formed from arachidonic acid either by 12-lipoxygenase or by a cytochrome P450 monooxygenase. 12-Lipoxygenase is generally localized in the soluble cytosolic fraction, and the cytochrome P450 monooxygenase is a microsomal enzyme. There are three isoforms of arachidonate 12-lipoxygenase in mammals: platelet, leukocyte, and epidermal types Inhibitors of 12-lipoxygenase may be of benefit for the treatment of hypertension and inflammation.

12-Lipoxygenase isolated from human platelets is used. Test compound or vehicle with 150 mg/ml enzyme‡ is preincubated for 15 minutes at 25° C. in modified Tris-HCl buffer pH 7.4. The reaction is initiated by addition of 30 mM arachidonic acid for another 15 minute incubation period. Enzyme activity is determined spectrophotometrically by measuring the formation of 12-HETE. Compounds are screened at 10 mM. Baicalein is used as the standard reference for this assay.

At 10 and 30 ug/ml, the percent inhibition of 12-lipoxygenase was comparable for all of Examples 1-4.

LTB4

Leukotriene (LT) receptors most sensitive to the endogenous ligand BLT$_4$ are named BLT receptors, whereas those preferentially activated by the CysLTs are named LTC$_4$, D$_4$ and E$_4$. LT receptors belong to the superfamily of G protein-coupled seven transmembrane proteins. G-protein-coupled receptors constitute one of the major signal transduction systems in eukaryotic cells. Coding sequences for these receptors, in those regions believed to contribute to the agonist-antagonist binding site, are strongly conserved across mammalian species. LTB$_4$ receptors are found in leukocytes, spleen and thymus and also reported to be present in peritoneal macrophages and eosinophils.

Human U-937 (histiocytic lymphoma) cells are used to prepare membranes in modified Tris-HCl buffer at pH 7.4. A 60 mg‡ aliquot is incubated with 0.2 nM [$^3$H] Leukotriene B$_4$ for 30 minutes at 25° C. Non-specific binding is estimated in the presence of 2 mM leukotriene B$_4$. Membranes are filtered and washed 3 times and the filters are counted to determine [$^3$H] Leukotriene B$_4$ specifically bound. Compounds are screened at 10 µM.

At 10 ug/ml, the percent inhibition of Leukotriene B4 was higher for Examples 2-4 than for Example 1. At 30 ug/ml, the percent inhibition of Leukotriene B4 was higher for Example 4 than for Examples 1-3, higher for Example 3 than for Examples 1-2, and higher for Example 2 than for Example 1.

PGE2

Tert-Keratinocytes are plated out and are supplemented with arachidonic acid upon treatment with dilutions of Zyflamend or DMSO control. The DMSO content is kept at 0.1% in all groups. 20 Hours post-treatment, the supernatants are collected for PGE2 determination. The cells are assessed for viability using the Cell Titer Glo system (Promega) according to manufacturer instructions. The ATP values are normalized to the values from the DMSO-treated group. Prostaglandin E2 (PGE2) levels are determined using the PGE2 Assay Kit from CisBio according to directions. PGE2 values are normalized to the corresponding ATP levels and are expressed as a % of PGE2 produced by DMSO-treated control. As can be seen in table and graph below, dilutions of Zyflamend exhibit a dose-response inhibition of PGE2 production with an estimated IC50 occurring near 1,250,000 dilution. Zyflamend is clearly demonstrating an anti-inflammatory effect that is easily detectable using the PGE2 assay in keratinocytes.

The IC50 (w/v %) for inhibition of PGE2 Release was comparable for all of Examples 1-4.

NFkB

A Nuclear Factor kappa-light-chain-enhancer of activated B cells (NFkB) reporter system detected by beta-lactamase activity was purchased from Invitrogen. The substrate system (ToxiBlazer) is also purchased from Invitrogen and used per instructions. Cells are plated and treated with Zyflamend dilutions and controls for 30 minutes before being stimulated with Tumor Necrosis Factor alpha (TNFα). After 4.5 hours, the ToxiBlazer substrate is added and incubated for 2 more hours. The various fluorescent output at the prescribed wavelengths are then measured using an Envision Plate reader. We found that the ToxiBlazer cytoxicity system signal was interfered with by the Zyflamend (run 1) so we use the Cell Titer Glo system to measure viability (run 2). Data was kept when the ATP measured was ≥80% of the amount measured in the DMSO-treated control. As can be seen in both assay runs, the Zyflamend is inhibiting the TNFα-induced NFkB activation with an apparent IC50 near 1,562,500 dilution.

The IC50 (w/v %) for NF-kβ activation was lower for Examples 2-4 than for Example 1, and lower for Examples 2-3 than for Example 4.

COX-2

The COX-2 assay was an enzyme based assay. The kit used measures the peroxidase activity of COX. The peroxidase activity is assayed colorimetrically by monitoring the appearance of oxidized N,N,N',N'-tetramethyl-p-phenylenediamine (TMPD) at 590 nm. The kit includes isozyme-specific inhibitors for distinguishing COX-2 activity from COX-1 activity.

The IC50 (w/v %) for COX-2 inhibition was lower for Examples 2-3 than for Examples 1-4. The IC50 (w/v %) for COX-2 inhibition was comparable, but slightly higher, for Example 4 than for Example 1.

The active ingredients (amounts listed in milligrams) of any of examples 2-4 can be combined with a carrier into a softgel, tablet, capsule, or other form suitable for oral administration. The oral dosage form may be intended for administration once daily, or twice daily, or three or more times daily. In preferred forms, the oral dosage form is intended for administration once or twice daily. The carrier may be any inert or pharmaceutically acceptable carrier, as known in the art. The active ingredients of any of examples 2-4 can be incorporated into a food product, such as snack bars, candies, lozenges, beverages, and the like.

The active ingredients of any of examples 2-4 can be combined with a food for companion animals. The companion animal food may be complete and nutritionally balanced. The companion animal food may be raw or may be cooked, as by extrusion, steam, boiling, ohmic heating, retort, baking, frying or combinations thereof.

The active ingredients of any of examples 2-4 can be combined with a food, beverage, or other composition intended for ingestion. For example, the active ingredients of any of examples 2-4 can be combined with a meal-replacement beverage, a milk shake, juice, a juice-containing beverage, or a juice-flavored beverage. The active ingredients of any of examples 2-4 can be combined with a snack bar, such as a meal replacement bar, candy bar, energy bar, or the like.

A composition comprising the active ingredients of any of examples 2-4 may be free of inhibitors of inflammation recognized as drugs, such as meclofenamic acid, niflumic acid, indomethacin, mefenamic acid, phenylbutazone, alclofenac, aspirin, paracetamol, steroids, salicylate, prostacyclin, aurothiomalate, aurothioglucose, colchicines, ibuprofen, ketoprofen, naproxen sodium, or combinations thereof. A composition comprising the active ingredients of any of examples 2-4 may be substantially free of pharmacologically active inhibitors of inflammation. For example, a composition comprising the active ingredients of any of examples 2-4 may comprise less than 5%, or less than 3%, or less than 1% by weight of the composition inhibitors of inflammation recognized as drugs.

A composition comprising the active ingredients of any of examples 2-4 may be free of certain herbal inhibitors of inflammation, including hu zhang (*Polygonum cuspidatum*), Chinese goldthread (*Coptis chinensis*), barberry (*Berberis vulgaris*), Chinese skullcap (*Scutellaria baicalensis*), or combinations thereof. A composition comprising the active ingredients of any of examples 2-4 may be substantially free of certain herbal inhibitors of inflammation, including hu zhang, Chinese goldthread, barberry, Chinese skullcap, or combinations thereof. For example, a composition comprising the active ingredients of any of examples 2-4 may comprise less than 5%, or less than 3%, or less than 1% by weight of the composition certain herbal inhibitors of inflammation, including hu zhang, Chinese goldthread, barberry, Chinese skullcap, or combinations thereof. These herbal inhibitors may be excluded as whole herbs or plant parts, extracts, powders, concentrates, or combinations thereof.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm."

Every document cited herein, including any cross referenced or related patent or application and any patent application or patent to which this application claims priority or benefit thereof, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. An oral dosage form for maintaining healthy immune response, the oral dosage form comprising about 100 mg supercritical extract of rosemary; about 50 mg hydroethanolic extract of rosemary; about 22 mg supercritical extract of turmeric; about 88 mg hydroethanolic extract of turmeric; about 100 mg extract of green tea; about 54 mg supercritical extract of ginger; about 46 mg hydroethanolic extract of ginger; about 42 mg hydroethanolic extract of holy basil; about 8 mg supercritical extract of holy basil; about 10 mg supercritical extract of oregano; about 10 mg hydroethanolic extract of oregano; about 7 mg supercritical extract of clove; about 10 mg supercritical extract of thyme; about 30 mg black currant; and a carrier.

2. The oral dosage form of claim 1, wherein the supplement is substantially free of hu zhang extract.

3. The oral dosage form of claim 2, further comprising boswellia *serrata*.

4. An oral dosage form for maintaining healthy immune response, the oral dosage form comprising about 100 mg supercritical extract of rosemary; about 50 mg hydroethanolic extract of rosemary; about 22 mg supercritical extract of turmeric; about 88 mg hydroethanolic extract of turmeric; about 100 mg extract of green tea; about 54 mg supercritical extract of ginger; about 46 mg hydroethanolic extract of ginger; about 42 mg hydroethanolic extract of holy basil; about 8 mg supercritical extract of holy basil; about 10 mg supercritical extract of oregano; about 10 mg hydroethanolic extract of oregano; about 7 mg supercritical extract of clove; about 5 mg to about 10 mg supercritical extract of thyme; about 30 to about 50 mg black currant; and a carrier.

5. An oral dosage form for maintaining healthy immune response, the oral dosage form comprising about 100 mg supercritical extract of rosemary; about 50 mg hydroethanolic extract of rosemary; about 25 mg supercritical extract of turmeric; about 100 mg hydroethanolic extract of turmeric; about 100 mg extract of green tea; about 15 mg supercritical extract of ginger; about 60 mg hydroethanolic extract of ginger; about 42 mg hydroethanolic extract of holy basil; about 8 mg supercritical extract of holy basil; about 10 mg supercritical extract of oregano; about 10 mg hydroethanolic extract of oregano; about 7 mg supercritical extract of clove; about 30 mg black currant; and a carrier.

6. The oral dosage form of claim 5 further comprising about 4 mg supercritical extract of chamomile and about 11 mg hydroethanolic extract of chamomile.

7. The oral dosage form of claim 5 further comprising about 150 mg boswellia *serrata*.

8. A method of moderating the inflammatory response to a transient pro-inflammatory stimulus, comprising administering the oral dosage form of claim 1 to a mammal prior to the mammal encountering the stimulus.

9. The method of claim 8, wherein the transient pro-inflammatory stimulus is selected from the group consisting of exercise, an allergen, a transient increase in oxidative stress, and combinations thereof.

10. A method of moderating the inflammatory response to a transient pro-inflammatory stimulus, comprising administering the oral dosage form of claim 4 to a mammal prior to the mammal encountering the stimulus.

11. The method of claim 10, wherein the transient pro-inflammatory stimulus is selected from the group consisting of exercise, an allergen, a transient increase in oxidative stress, and combinations thereof.

* * * * *